Nov. 30, 1948. E. S. BOERNER Plant Pat. 812
ROSE PLANT
Filed May 13, 1947
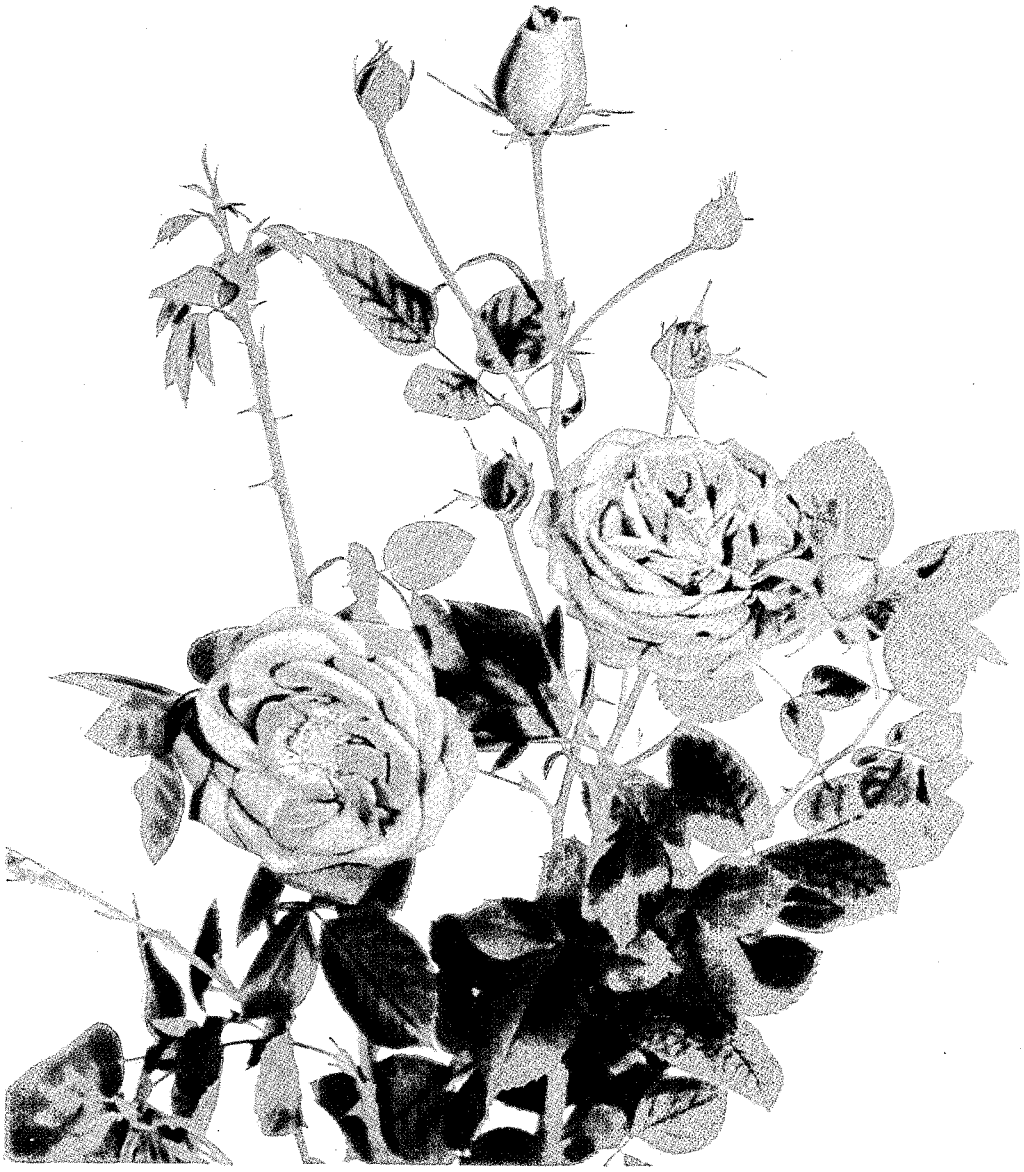
Inventor
E. S. Boerner
by Robb & Robb
attorneys Patented Nov. 30, 1948

Plant Pat. 812

UNITED STATES PATENT OFFICE

812

ROSE PLANT

Eugene S. Boerner, Newark, N. Y., assignor to Jackson & Perkins Company, Newark, N. Y., a corporation of New York Application May 13, 1947, Serial No. 747,699

1 Claim. (Cl. 47—61)

The present invention relates to a new and distinct variety of rose plant in the class of large flowered polyanthas resulting from a cross of an unnamed yellow "Pinocchio" seedling and "Donald Prior" (Pl. Pat. #377).

This new rose displays a distinct combination of certain characteristics possessed by its parents, greatly improving upon them in respect to color of flowers and habits of growth. More specifically, the flowers of this new variety are of bright Carmine instead of Geranium Pink of "Pinocchio" (Pl. Pat. #484), but the blooms take the shape of the latter variety. However, the new variety retains the characteristic found in "Pinocchio" of deepening of the color as the bloom grows older.

In habits of growth, this new variety combines the upright characteristic of "Pinocchio" with the bushiness of "Donald Prior," and its foliage displays a combination of the characteristics of the foliage of these two varieties.

A further unique characteristic is noted in connection with its filaments which are of two colors, Pale Greenish Yellow at the base and Begonia Rose near the anthers.

Asexual reproduction of this new variety shows the foregoing characteristics come true to form and are established.

The accompanying drawing discloses specimens of this new variety showing clearly the development of the flower from bud to full blown stages of development, the characteristics of the foliage, thorns, etc.

The following is a detailed description of the new variety, color terminology being in accordance with Ridgway's Color Standard:

Parentage: Seedling.

*Seed parent.*—Yellow Pinocchio seedling (unpatented).

*Pollen parent*—"Donald Prior."

Classification:

*Botanic.*—Large flowered polyantha.

*Commercial.*—Floribunda.

*Flower*

(Observations made in the greenhouse of Jackson & Perkins Company, Newark, New York, in the month of December.)

Blooming Habit: Recurrent—continuous.

Bud:

*Size.*—Medium.

*Form.*—Ovoid. Is not affected by wet or hot weather.

*Color.*—When sepals first divide—Hay's Maroon, Plate 13; when petals begin to unfurl—Bordeaux, Plate 12; when half blown—inside of petals, Pomegranate Purple, Plate 12, overlaid with Carmine, Plate 1; reverse of petals, Carmine, Plate 1, lightly overcast with Oxblood Red, Plate 1.

*Sepals.*—Serrated, branched, "hood" above bud. Curl back when petals begin to unfurl. Color—inside—Kildare Green, Plate 31; outside—Parrot Green, Plate 6.

*Calyx.*—Shape—pear. Size—small. Aspect—smooth. Odor when rubbed—none. Color—Parrot Green, Plate 6.

*Peduncle.*— Length — medium. Aspect — prickly. Color—Parrot Green, Plate 6 Strength—bending.

*Opening.*—Opens up well. Is not affected by adverse weather conditions.

Bloom:

*Size.*—Medium. Average size when fully expanded, 3½".

*Borne.*—Several together, in clusters. In clusters—pyramidal.

*Stems.*—Medium length; normal.

*Form.*—When first open, cupped. Permanence—retains its form to the end.

*Petalage.*—Double (full but open center). Number of petals under normal conditions, 25 to 30.

*Color.*—Center of flower—Pomegranate Purple, Plate 12, overcast with Tyrian Red, Plate 12. Outer petals—Carmine, Plate 1, overlaid with Rose Red, Plate 12. Base of petals (aiglet)—Pale Lumiere Green, Plate 17. Inside of petals—Carmine, Plate 1, overlaid with Rose Red, Plate 12. Reverse of petals—Pomegranate Purple, Plate 12, lightly overcast with Bordeaux, plate 12. General tonality from a distance—Carmine, Plate 1, overcast with Pomegranate Purple, Plate 12.

*Discoloration.*—General tonality at end of first day—Carmine, Plate 1, overlaid with Pomegranate Purple, Plate 12. Second day—Pomegranate Purple, Plate 12, overcast with Rose Red, Plate 12. Third day—Pomegranate Purple, Plate 12, overcast with Rose Red, Plate 12.

Petals:

*Texture.*—thick. Is not affected by wet or hot weather.

*Appearance.*—Inside — velvety; outside — satiny.

*Form.*—Round.

*Arrangement.*—Imbricated (regularly arranged shingle-like). Petaloids in center—few; small.

*Persistence.*—Drop off cleanly.
*Fragrance.*—Moderate. Nature—wild rose.
*Lasting quality.*—On the plant and as cut flower—long.

Genital organs:
*Stamens.*—*Anthers*—medium size; many. Color—Apricot Yellow, Plate 4. Arrangement—regular around styles. *Filaments (threads)*—medium length. Color—lower half, Pale Greenish Yellow, Plate 5; upper half, Begonia Rose, Plate 1.
*Pollen.*—Light Cadmium, Plate 4.
*Styles.*—Bunched, uneven length; medium length; thin.
*Stigmas.*—Light Orange Yellow, Plate 3.
*Ovaries.*—All enclosed in calyx.

*Plant*

Form: Bush.
Growth: Vigorous; upright; branching.
Foliage: Five to seven leaflets.
*Size.*—Medium.
*Quantity.*—Normal.
*Color.*—New foliage: upper side—Oil Green, Plate 5; serrations, Victoria Lake, Plate 1; under side—Victoria Lake, Plate 1. Old foliage: upper side—Spinach Green, Plate 5; under side—Light Cress Green, Plate 31.
*Shape.*—Oval pointed.

*Texture.*—Upper side—leathery; under side—smooth. Ribs and veins—prominent.
*Edge.*—Serrated (saw toothed).
*Serration.*—Single; small.
*Leaf stem.*—Cerro Green, Plate 5. Under side—prickles.
*Stipules.*—Medium length; serrated.
*Disease resistance.*—Resistant.

Wood:
*New wood.*—Light Yellowish Olive, Plate 30. Bark—smooth.
*Old wood.*—Light Elm Green, Plate 17. Bark—smooth.

Thorns:
*Thorns.*—Quantity—on main stalks from base, and on laterals from stalk—ordinary. Form—narrow base; medium length; straight. Color when young—Eugenia Red, Plate 13. Position—irregular.
*Prickles and short needles.*—None.

I claim:

A new and distinct variety of rose plant, characterized as to novelty by the shape of its blooms and their habit of deepening in color as the bloom grows older, its habit of upright growth and bushiness, and its foliage and filament coloring, substantially as shown and described.

EUGENE S. BOERNER.

No references cited.